United States Patent [19]

Jariabka

[11] 4,202,330
[45] May 13, 1980

[54] LIFE SUPPORT SYSTEM AND VALVE FOR USE THEREWITH

[76] Inventor: Daniel S. Jariabka, 1998 Big Oak La., Northbrook, Ill. 60062

[21] Appl. No.: 919,072

[22] Filed: Jun. 26, 1978

[51] Int. Cl.² ............................................. A61M 16/00
[52] U.S. Cl. .......................... 128/204.18; 137/625.69; 128/205.24; 128/207.14; 128/207.16
[58] Field of Search ............... 128/145.8, 145.6, 145.5, 128/145.7, 203, 208, 351; 137/625.69

[56] References Cited

U.S. PATENT DOCUMENTS

| | | | |
|---|---|---|---|
| 374,402 | 12/1887 | Fell | 128/145.7 |
| 1,848,232 | 3/1932 | Swope et al. | 128/145.8 |
| 3,279,748 | 10/1966 | Coulter | 137/625.69 X |

FOREIGN PATENT DOCUMENTS 1212708   3/1960   France ................................. 128/145.8

*Primary Examiner*—Henry J. Recla

[57] ABSTRACT

This invention relates generally to the art of providing a method and apparatus having a source of breathable gas connected to a tracheal tube via a manually operable valve for performing an emergency traecheostomy and, particularly, to performing an emergency traecheostomy under field conditions such as those typically encountered by a paramedic or like individual.

3 Claims, 3 Drawing Figures

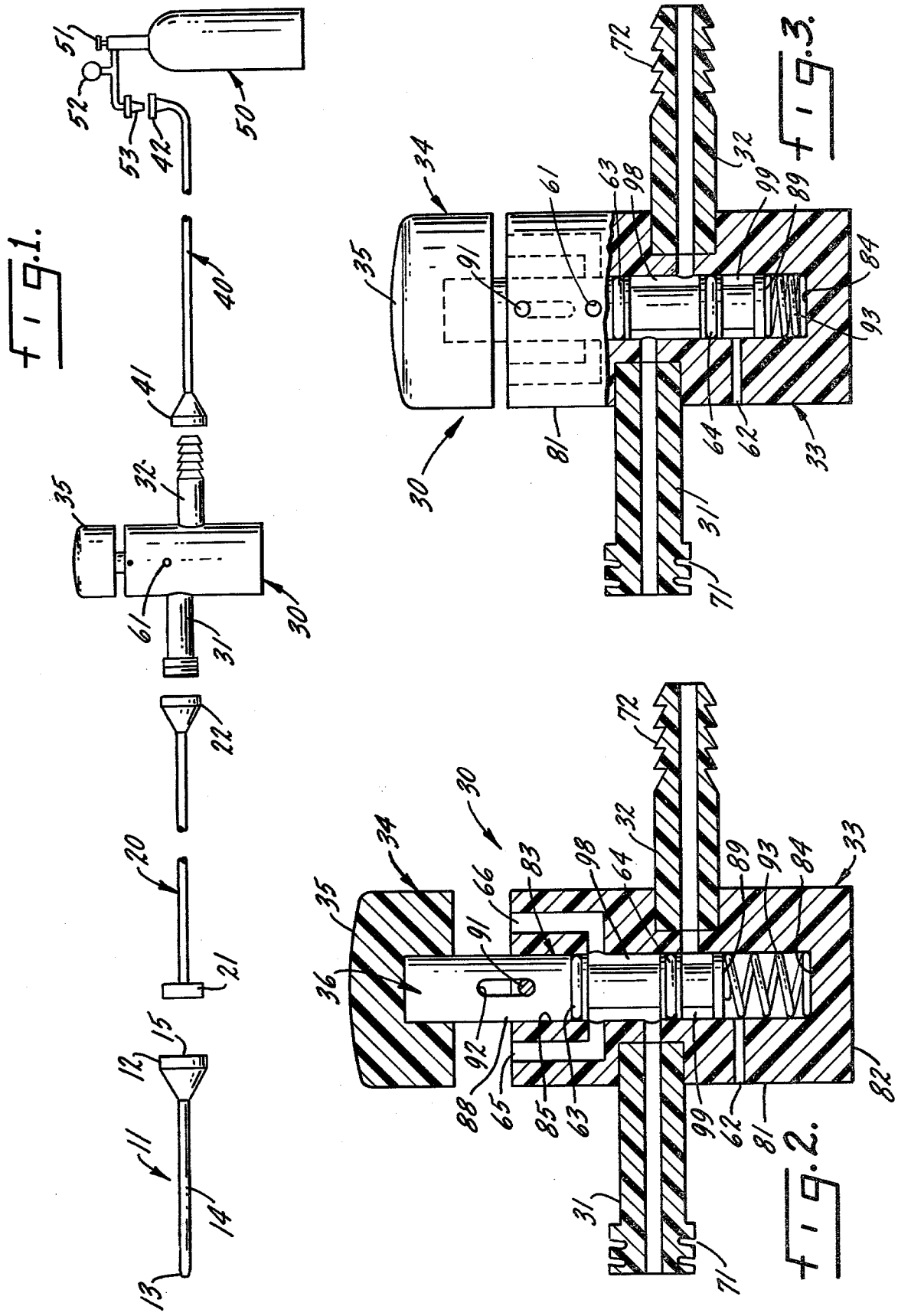

LIFE SUPPORT SYSTEM AND VALVE FOR USE THEREWITH

BACKGROUND OF THE INVENTION

Various devices and method for performing a traecheostomy have been proposed, but all have had significant disadvantages. The majority of these devices are designed for use under quiescent conditions, such as in a hospital operating room, and are completely inappropriate or not always adaptable for use in emergency field conditions or adverse situations.

Other devices which have been proposed for use under field conditions also have numerous disadvantages. In particular, many do not afford the operator or paramedic sufficient flexibility to use the device on a victim who may be frantic and difficult to control. Others do not provide means for introducing and regulating the flow of a high concentration of oxygen at generally low pressure into the lungs of a stricken patient and permitting the exhalation of air by the patient through the apparatus.

SUMMARY OF THE INVENTION

Accordingly, a primary object of this invention is to overcome these disadvantages and provide a life support system for use in emergency conditions whereby suitably formed insertions means may be inserted into the trachea through the cricoid of a striken patient and first conduit means connect said insertion means to valving means which, in turn, is connected by second conduit means to a suitable oxygen source, such as an oxygen tank, and the valving means controls the flow of a high concentration of oxygen at generally low pressure into the patient and controls the exhalation of air by the patient.

Another object of the invention is to provide a life support system usuable under emergency field conditions whereby the insertion means is suitably formed so as to minimize blood loss.

Another object of the invention is to provide a life support system having flexible conduit means connected to valving means whereby the conduit means permits lateral and longitudinal movement of the valving means without causing dislodgement of the insertion means at the puncture site or disconnection of the conduit means from the other elements of the system.

Another object of the invention is to provide a life support system usable under emergency field conditions having valving means which is operable from a location remote from the immediate vicinity of the puncture site.

Another object of the invention is to provide manually operable valving means which is adaptable for use in a variety of life support systems whereby said valving means controls the flow of a high concentration of forced oxygen at generally low pressure into the patient and controls the exhalation of air by the patient through said valving means.

Yet another object of the invention is to provide a method for performing an emergency traecheostomy including the steps of inserting insertion insertion means into the trachea of a stricken patient, connecting first conduit means at one end to the base of said insertion means and at the other end to a first port of valving means, connecting second conduit means at one end to a second port of said valving means and at the other end to an oxygen supply source, and manually operating said valving means so as to control the flow of oxygen through said valving means into said stricken patient and control the exhalation of air by said patient through said valving means into the atmosphere.

Other objects and advantages of the invention will be apparent from a reading of the following exemplary description.

DESCRIPTION OF A SPECIFIC EMBODIMENT

The invention is illustrated more or less diagrammatically in the drawing wherein:

FIG. 1 is a diagrammatic view of the system of the invention with parts broken away;

FIG. 2 is a cut-away view of the valving means of the invention showing the plunger means in a regular upward position; and FIG. 3 is a cut-away view of the valving means showing the plunger means in a downward position.

Like reference numerals will be used to refer to like components from figure to figure of the drawing.

The steps involved in performing the method of the invention are illustrated in FIG. 1. A preferred sequence includes cleansing the throat of the patient; inserting insertion means, shown generally at 11, into the trachea; placing a small amount of ointment, preferably germocidal ointment, around the insertion means near the puncture site; connecting a first conduit means, shown generally at 20, at one end 21 to the base 12 of the insertion means; connecting said first conduit means at the other end 22 to a first port 31 of a valving means, shown generally at 30; connecting a second conduit means, shown generally at 40 at one end 41 to a second port 32 of the valving means; connecting said second conduit means at the other end 42 to an oxygen supply source, shown generally at 50; and manually regulating the valving means so as to control the flow of oxygen into the trachea of the patient and control the flow of expired air from the patient into the atmosphere. It will be appreciated that other sequences of these steps are within the concept of the invention.

It will be noted that the insertion means 11 provides suitable means for supplying oxygen directly to the patient by by-passing occlusions in the mouth or upper throat area which prevent the normal passage of air. In a preferred embodiment, the insertion means may be a conventional catheter having a tip region 13, a body 14, a base region 12, and a hollow central region 15 disposed substantially about the longitudinal axis of the insertion means which permits the passage of oxygen through the insertion means into the patient and the passage of expired air from the patient. The tip region 13 is suitably shaped so that its insertion into the patient minimizes blood loss and permits stabilization of the insertion means in the patient during use of the invention. This stabilization can be augmented by conventional securement means, such as taping the insertion means to the patient.

The base region of the insertion means is suitably adapted to be connected to first conduit means 20 at one end thereof at 21. The other end 22 of the first conduit means is likewise connected to a first port 31 of the valving means of the invention. It will be appreciated that the first conduit means is made of a suitably flexible material, such as conventional plastic medical tubing, so as to permit lateral and longitudinal movement of the valving means during use without causing dislodgement of the first conduit means from either the insertion means or the valving means. Flexible conduit means also prevents the dislodgement of the insertion means at the puncture site. It will be appreciated that the first conduit means has a suitable length such that the valving means may be operated remotely from the puncture site so as to afford flexibility to the operator and to avoid interference by the patient.

The second conduit means 40 is similarly constructed of a suitably flexible material so as to accomplish the aforesaid objectives as well as to prevent the dislodgement of the second conduit means from the valving means or from the oxygen supply source. It will be noted that the second conduit means is adapted to be connected at one end 41 to a second port 32 of the valving means and at the other end 42 to the oxygen supply source 50.

Referring to FIGS. 2 and 3, it will be noted that ports 31 and 32 of the valving means are suitably shaped to receive the connections of the first and second conduit means. Threads 71 and 72 of the respective ports 31 and 32 secure said connections to prevent dislodgement thereof and to eliminate the escape of oxygen or air passing through the respective ports during use.

The oxygen supply source of the invention, shown generally at 50 in FIG. 1, may be a conventional oxygen tank having conventional valving means 51 to regulate the flow of oxygen from the tank and conventional gauging means 52. Port 53 of the oxygen supply source is suitably adapted to receive the connection of the second conduit means 40 at end 42.

The valving means of the invention is shown in FIGS. 2 and 3 and includes a housing, indicated generally at 33, ports 31 and 32 connected to said housing, and manually operable spring-biased plunger means shown generally at 34.

The housing may be constructed of a suitable non-deformable material, such as plastic, which will maintain its shape notwithstanding the existence of various apertures and passageways through its interior region. The exterior region of the housing is substantially cylinder-like, having a wall region 81 and base region 82. A generally cylindrical longitudinally oriented chamber 83 which is adapted to receive shaft 36 of the plunger means is disposed in the interior of the housing. Chamber 83 has a uniform internal wall region 85 and internal base 84.

In a preferred embodiment, the housing is adapted to be connected to ports 31 and 32 which are disposed on opposite sides of the wall region. However, it will be appreciated that in alternate embodiments, ports 31 and 32 may be integrally formed with said housing and said ports may be disposed other than on opposite sides of the wall region.

The plunger means of the invention, indicated generally at 34, includes a head 35 and a generally cylindrical shaft 36 connected to the head. In an alternate embodiment, the shaft may be integrally formed with the head. The plunger means may likewise be made of a suitable, substantially non-deformable material, such as plastic.

Shaft 36 of the plunger means is suitably shaped to be disposed within chamber 83 of the housing and moved or displaced longitudinally within said chamber. As illustrated in FIGS. 2 and 3, the shaft is generally cylindrical having a base region 89 and a wall region having zones 88, 98 and 99. Zone 88 defines the area of the wall region having a maximum uniform diameter and zones 98 and 99, respectively, define areas of the wall region having a reduced uniform diameter. The shaft is also adapted to receive a conventional O-ring or O-rings, such as 63 and 64.

It will be understood that longitudinal displacement of the shaft and, correspondingly, of the plunger means, in an upward direction is limited by pin 91 suitably disposed in slot 92 of the housing means. Longitudinal displacement of the shaft in a downward direction is limited by the force exerted upon base 89 of the shaft by spring means 93 disposed in the base region of chamber 83. Spring means 93 is suitably adapted to permit manual depression of the head of the plunger means to a suitably fixed downward position and, upon release thereof, to return the plunger means to its regular upward position.

FIG. 2 shows the plunger means in its regular upward position. It will be understood that in such position expired air flowing from the patient via the insertion means and first conduit means will enter port 31 and will be discharged into the atmosphere through the passageways created in the valving means by zone 98 of shaft 36 and exhaust channels 65 and 66. Exhaust channel 61 shown in FIG. 4 also assists the discharge of the expired air into the atmosphere through the valving means. O-rings 63 and 64 retain the expired air within the desired channels within the valving means. An oxygen drain channel 62 is also suitably provided to permit oxygen flowing into the valving means through port 32 to be discharged into the atmosphere via the passageway created by zone 99 of shaft 36.

FIG. 3 shows the plunger means in a downward position which is obtained by manually depressing head 35 against the force of spring means 93. It will be noted that when the plunger means is in this position, a high concentration of oxygen under low pressure will be permitted to flow through the passageway in the valving means created by zone 98 of shaft 36 and eventually into the patient via port 31, the first conduit means and the insertion means of the system.

It will thus be appreciated that the life support system illustrated provides a means for manually controlling the flow of oxygen into a patient and controlling the expiration of air by the patient under emergency conditions.

The system is especially adapted to be used in connection with supplying 100% oxygen from a conventional oxygen supply source at low pressure. Oxygen flow, preferably at 15 liters. Under these conditions, taking into consideration the rate of consumption of oxygen by a human patient, the plunger means of the invention need be depressed for approximately 2-3 seconds, 4 times a minute.

Although a preferred embodiment of the invention has been illustrated and described, it will be apparent from a reading of the foregoing description that the disclosure is exemplary only. Accordingly, it is intended that the scope of the invention be determined, not by the scope of the foregoing exemplary description, but solely by the scope of the hereafter appended claims when interpreted in light of the prior art.

What is claimed is:

1. In a life support system for use in performing an emergency tracheostomy on a patient, including a manually operable, small, portable valve connected between a first conduit means and a second conduit means where said first conduit means is further connected to insertion means for being inserted into the throat region of the patient and for passing gas therethrough and where said second conduit means is further connected to a supply of oxygen; the improvement comprising:

said valve including a housing having an interior surface defining a chamber therein oriented about a longitudinal axis and having an open end communicating with the exterior of said housing and a closed end opposite said open end;

said housing defining a first port for providing communication between said chamber and said first conduit for alternately passing oxygen flow to said patient and passing expiration air flow from said patient;

said housing further defining a second port for providing communication between said chamber and said second conduit for passing oxygen from said oxygen supply to said chamber, said second port being spaced from said first port at the interior surface of said chamber by a predetermined amount along the longitudinal axis of the chamber between said first port and said chamber closed end;

said housing further defining a patient expiration air exhaust channel communicating between the exterior of said housing and said chamber and terminating in an exhaust aperture in said chamber located between said chamber open end and said first port;

said housing further defining an oxygen drain channel communicating between the exterior of said housing and said chamber and terminating in a drain aperture in said chamber located between the closed end of said chamber and said second port;

a plunger slidably disposed within said chamber for movement between a patient air expiration position and a patient oxygen supply position, said plunger including spaced-apart first and second seal means for sealing between said plunger and the interior surface of said chamber, said first and second seal means defining them a central flow passageway in said valve, said second seal means being disposed between said first seal means and the closed end of said chamber for defining an end flow passageway in said valve adjacent said central flow passageway;

spring means disposed within said chamber at the closed end thereof for urging said plunger outwardly through said open end of said chamber to said patient oxygen supply position;

stop means mounted in said housing for limiting at least the outward movement of said plunger under the influence of said spring;

said predetermined port spacing amount being sufficient to accommodate the simultaneous location of (1) said first seal means between said exhaust channel aperture and said chamber open end and (2) said second seal means between the first and second ports when the plunger is biased to the patient air expiration position whereby oxygen flowing into said valve second port and accumulating in said closed end of said chamber can leak out of said end flow passageway through said oxygen drain channel and whereby the expiration of air from the patient can flow sequentially through said insertion means, through said first conduit and first port, through said central passageway, and out of said valve through said exhaust channel; and said predetermined port spacing amount being also sufficient, when said plunger is pressed inwardly to said patient oxygen supply position, to accommodate the simultaneous location of (1) said first seal means between said exhaust channel and said first port and (2) said second seal means between said second port and said oxygen drain channel whereby oxygen from said oxygen supply can flow sequentially through said second conduit and second port, through said central passageway, out of said valve through said first port, through said first conduit, and finally through said insertion means into said patient.

2. The life support system in accordance with claim 1 in which said chamber has a generally cylindrical configuration, in which said plunger is a generally cylindrical member, and in which said first and second seal means are generally annular flanges formed of resilient material.

3. The life support system in accordance with claim 1 in which said plunger defines a slot formed therethrough outwardly of said first seal means and in which said stop means includes a cross member disposed within said slot and connected to opposite sides of said chamber.

* * * * *